(12) United States Patent
Abe

(10) Patent No.: US 10,544,171 B2
(45) Date of Patent: Jan. 28, 2020

(54) PROCESS FOR PRODUCING CYCLIC HYDROGENATED SILANE COMPOUND

(71) Applicant: NIPPON SHOKUBAI CO., LTD., Osaka (JP)

(72) Inventor: Takashi Abe, Osaka (JP)

(73) Assignee: NIPPON SHOKUBAI CO., LTD, Osaka (JP)

( * ) Notice: Subject to any disclaimer, the term of this patent is extended or adjusted under 35 U.S.C. 154(b) by 0 days.

(21) Appl. No.: 15/919,573

(22) Filed: Mar. 13, 2018

(65) Prior Publication Data

US 2019/0284214 A1  Sep. 19, 2019

(51) Int. Cl.
C07F 7/21 (2006.01)
(52) U.S. Cl.
CPC ..................................... *C07F 7/21* (2013.01)
(58) Field of Classification Search
None
See application file for complete search history.

(56) References Cited

U.S. PATENT DOCUMENTS

| | | | |
|---|---|---|---|
| 5,942,637 | A | 8/1999 | Boudjouk et al. |
| 2002/0076378 | A1 | 6/2002 | Wolfe et al. |
| 2012/0294791 | A1 | 11/2012 | Elangovan et al. |
| 2014/0012029 | A1 | 1/2014 | Abe et al. |
| 2014/0012030 | A1 | 1/2014 | Abe et al. |
| 2016/0311692 | A1* | 10/2016 | Kitamura .......... C01B 33/10773 |
| 2017/0349444 | A1 | 12/2017 | Wagner et al. |

FOREIGN PATENT DOCUMENTS

| | | |
|---|---|---|
| JP | 4519955 | 8/2010 |
| JP | 2014-12647 | 1/2014 |
| JP | 2014-12648 | 1/2014 |
| WO | 2011/094191 | 8/2011 |
| WO | 2016/095898 | 6/2016 |

OTHER PUBLICATIONS

Shimoda et al., "Solution-processed silicon films and transistors", Nature, vol. 440, Apr. 6, 2006, pp. 783-786.
Hengge et al., "Preparation of Cyclohexasilane, $Si_6H_{12}$", Angew. Chem. Int. Ed. Engl., vol. 16, No. 6, 1977, p. 403.
Tillmann et al., "Lewis Acidity of $Si_6cl_{12}$ and Its Role as Convenient $S_iCl_2$ Source", Inorg. Chem., vol. 54, 2015, pp. 9611-9618.
Notification of Reasons for Rejection dated Jun. 11, 2019 in Japanese Application No. 2015-231143, with English translation.
Dai et al., "'Inverse Sandwich' Complexes of Perhalogenated Cyclohexasilane", Organometallics, vol. 29, 2010, pp. 2203-2205.

* cited by examiner

*Primary Examiner* — Clinton A Brooks
*Assistant Examiner* — Kofi Adzamli
(74) *Attorney, Agent, or Firm* — Wenderoth, Lind & Ponack, L.L.P.

(57) ABSTRACT

A process for producing a cyclic hydrogenated silane compound comprising: a decomplexation step of contacting a salt of a cyclic halosilane compound with a Lewis acid compound to react, thereby obtaining a cyclic halosilane compound; and a reduction step of contacting the cyclic halosilane compound with a metal hydride to reduce the cyclic halosilane compound, thereby obtaining a cyclic hydrogenated silane compound.

8 Claims, No Drawings

PROCESS FOR PRODUCING CYCLIC HYDROGENATED SILANE COMPOUND

STATEMENT REGARDING PRIOR DISCLOSURES BY THE INVENTOR OR A JOINT INVENTOR

The invention of the present application is disclosed in Japanese Unexamined Patent Publication No. 2017-95324, a prior disclosure made by the inventor in a grace period, that does not constitute a prior art to the invention of the present application.

BACKGROUND OF THE INVENTION

Field of the Invention

The present invention relates to a process for producing a cyclic hydrogenated silane compound.

Description of the Related Art

Thin film silicon is used for applications such as solar cells and semiconductors, and this thin film silicon has been conventionally prepared by a chemical vapor deposition method (CVD method) using a monosilane as a raw material. In recent years, a new producing method using a hydrogenated polysilane has attracted attention instead of the CVD method. This producing method is a coating film-forming method (a liquid process) in which a hydrogenated polysilane solution is applied to a substrate and then is calcinated, and cyclopentasilane, which is a cyclic hydrogenated silane, is used as a raw material for the hydrogenated polysilane solution. It has been reported that the cyclopentasilane is converted to a hydrogenated polysilane by UV irradiation (T. Shimoda et al., "Solution-processed silicon films and transistors", Nature, vol. 440, p. 783 (2006)).

There is a possibility that a hydrogenated polysilane is synthesized also by using a cyclic hydrogenated silane compound other than cyclopentasilane as a raw material. As a cyclic hydrogenated silane compound, cyclohexasilane is known, other than cyclopentasilane. As a process for producing cyclohexasilane, for example, Japanese Patent No. 4519955 and WO 2011/094191 disclose a process for producing cyclohexasilane comprising the steps of preparing a salt of a halogenated cyclohexasilane dianion by contacting trichlorosilane with a tertiary polyamine such as N, N, N', N'', N''-pentaethyl diethylenetriamine (pedeta) or N, N, N', N'-tetraethyl ethylenediamine (teeda) to conduct cyclization coupling, and reducing it with a metal hydride. Japanese Unexamined Patent Publications No. 2014-12647 and No. 2014-12648 disclose a process for producing cyclohexasilane comprising the steps of preparing a salt of a halogenated cyclohexasilane dianion by contacting trichlorosilane with a phosphonium salt or an ammonium salt to conduct cyclization coupling, and reducing it with a metal hydride. E. Hengge et al. ("Preparation of cyclohexasilane, $Si_6H_{12}$", Angew. Chem. Int. Ed. Engl., 16, p. 403 (1977)) discloses a process for producing cyclohexasilane comprising the steps of preparing dodecaphenylcyclohexasilane by reacting $Ph_2SiCl_2$ with an alkali metal to conduct cyclization coupling, reacting it with aluminum chloride to give dodecachlorocyclohexasilane, and reducing it with a metal hydride. J. Tillmann et al. ("Lewis acidity of $Si_6Cl_{12}$ and its role as convenient $SiCl_2$ source", Inorganic Chemistry, vol. 54, p. 9611 (2015)) discloses a process for producing dodecachlorocyclohexasilane comprising the steps of preparing a salt of a halogenated cyclohexasilane dianion by contacting hexachlorodisilane with a tetra-n-butylammonium salt to conduct cyclization coupling, and reacting it with aluminum chloride which is a Lewis acid, though it is not a process for producing cyclohexasilane.

As described above, conventionally, various processes for producing cyclic hydrogenated silane compounds or cyclic halosilane compounds have been proposed, and there is a demand for a process for more easily and efficiently producing a cyclic hydrogenated silane compound. The present invention has been made in view of the above circumstances, and an object of the present invention is to provide a process for efficiently producing a cyclic hydrogenated silane compound.

SUMMARY OF INVENTION

One embodiment of a process for producing a cyclic hydrogenated silane compound of the present invention that solves the above problems comprises: a decomplexation step of contacting a salt of a cyclic halosilane compound with a Lewis acid compound to react, thereby obtaining a cyclic halosilane compound; and a reduction step of contacting the cyclic halosilane compound with a metal hydride to reduce the cyclic halosilane compound, thereby obtaining a cyclic hydrogenated silane compound. According to the producing process of the present invention, when a salt of a cyclic halosilane compound is brought into contact with a Lewis acid compound to be reacted, a noncomplexed cyclic halosilane compound, which has high solvent solubility (or dispersibility), can be obtained. Therefore, by contacting the noncomplexed cyclic halosilane compound with a metal hydride, reduction of the cyclic halosilane compound is able to be carried out in high concentration, and the cyclic hydrogenated silane compound can be efficiently produced.

In the reduction step, it is preferable that the cyclic halosilane compound is blended with a solvent so that a concentration of the cyclic halosilane compound is 0.02 mol/L or higher and is contacted with the metal hydride. It is also preferable that a used amount of the metal hydride is adjusted so that an equivalent of hydride of the metal hydride to one silicon-halogen bond contained in the cyclic halosilane compound is 0.5 equivalent or more and 15 equivalents or less. A total concentration of the cyclic halosilane compound and the cyclic hydrogenated silane compound in a reaction solution at the end of the reduction reaction is preferably 0.02 mol/L or higher and 1 mol/L or lower.

It is preferable that the producing process of the present invention further comprises a step of contacting a halogenated monosilane compound with at least one of a phosphonium salt and an ammonium salt to obtain the salt of the cyclic halosilane compound. The thus obtained salt of the cyclic halosilane compound has a phosphonium ion or an ammonium ion as a counter cation, and therefore, when it is reacted with the Lewis acid compound, formation of the cyclic halosilane compound is facilitated while suppressing generation of pyrophoric silane gas. In addition, the thus obtained salt of the cyclic halosilane compound can be made not contain a silicon atom other than the silicon atom constituting the ring structure, due to the use of a halogenated monosilane compound; and therefore, when the salt of the cyclic halosilane compound is reacted with the Lewis acid compound, side reactions such as a coupling reaction of the cyclic halosilane compound and generation of silane gas are suppressed. Further, storage stability of the salt of the cyclic halosilane compound and the cyclic halosilane compound can be improved. Therefore, the cyclic halosilane compound and the cyclic hydrogenated silane compound can be obtained in high yield.

The Lewis acid compound is preferably at least one compound selected from the group consisting of boron halide, aluminum halide, gallium halide, indium halide, thallium halide, copper halide, silver halide, gold halide, titanium halide, zirconium halide, iron halide, zinc halide and calcium halide.

It is preferable that the salt of the cyclic halosilane compound is a compound represented by the following formula (1). In the formula (1), $X^1$ and $X^2$ each independently represent a halogen atom; L represents an anionic ligand; p is an integer of −2 to 0 as a valence of the ligand L; K represents a counter cation; q is an integer of 0 to 2 as a valence of the counter cation K; n is an integer of 0 to 5; a, b and c are integers of 0 to 2n+6, wherein a+b+c=2n+6 but a and c are not simultaneously 0; d is an integer of 0 to 3, wherein a and d are not simultaneously 0; e is an integer of 0 to 3, wherein d+e=3; m is a number of 1 to 2; s is an integer of 1 or more; and t is an integer of 1 or more.

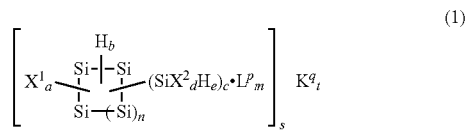

(1)

It is preferable that the cyclic halosilane compound is a compound represented by the following formula (6). In the formula (6), $X^1$, $X^2$, a to e and n represent the same meanings as the above.

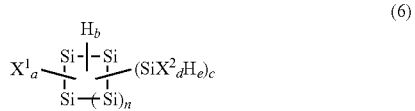

(6)

It is preferable that the metal hydride is at least one compound selected from the group consisting of an aluminum hydride compound, a boron hydride compound, a tin hydride compound and a hydrogenated transition metal compound.

As described above, according to the producing process of the present invention, a salt of a cyclic halosilane compound is brought into contact with a Lewis acid compound to react, whereby a noncomplexed cyclic halosilane compound, which has high solvent solubility (or dispersibility), can be obtained. Therefore, by contacting the noncomplexed cyclic halosilane compound with a metal hydride, reduction of the cyclic halosilane compound is able to be carried out in high concentration, and the cyclic hydrogenated silane compound can be efficiently produced.

DESCRIPTION OF THE PREFERRED EMBODIMENTS

A process for producing a cyclic hydrogenated silane compound of the present invention comprises a reduction step of contacting a cyclic halosilane compound with a metal hydride to reduce the cyclic halosilane compound, and preferably further comprises a decomplexation step of contacting a salt of a cyclic halosilane compound with a Lewis acid compound, thereby obtaining the cyclic halosilane compound. According to the process for producing a cyclic hydrogenated silane compound of the present invention, a cyclic hydrogenated silane can be efficiently produced.

As the salt of the cyclic halosilane compound used in the decomplexation step, a compound having a cyclic halosilane structure, in which silicon atoms are linked to form a homocyclic ring and a halogen atom is bonded to at least one silicon atom constituting the homocyclic ring, and forming a salt, is preferably used.

A number of silicon atoms constituting the homocyclic ring is not particularly limited, and is preferably 3 or more, more preferably 4 or more, even more preferably 5 or more, and preferably 8 or less, more preferably 7 or less, even more preferably 6 or less. The cyclic halosilane compound may contain a silicon atom not constituting the homocyclic ring, and for example, a substituent containing a silicon atom (e.g., a silyl group) may be bonded to a silicon atom constituting the homocyclic ring. However, it is preferable that the cyclic halosilane compound does not contain a silicon atom which does not constitute the homocyclic ring as much as possible. This is because when the a silicon atom which does not constitute the homocyclic ring is contained, the amount of silane gas generated tends to increase in storage of the salt of the cyclic halosilane compound or the cyclic halosilane compound or in the reduction step of the cyclic halosilane compound, and the yield in reduction of the cyclic halosilane compound tends to decrease.

It is preferable that at least one halogen atom is bonded to the homocyclic ring formed from silicon atoms, more preferably one or two halogen atoms (preferably two halogen atoms) are bonded to each of the silicon atoms constituting the homocyclic ring.

As the salt of the cyclic halosilane compound, a compound represented by the following formula (1) is preferably used.

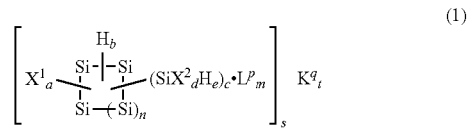

(1)

In the above formula (1), $X^1$ and $X^2$ each independently represent a halogen atom; L represents an anionic ligand; p is an integer of −2 to 0 as a valence of the ligand L; K represents a counter cation; q is an integer of 0 to 2 as a valence of the counter cation K; n is an integer of 0 to 5; a, b and c are integers of 0 to 2n+6, wherein a+b+c=2n+6 but a and c are not simultaneously 0; d is an integer of 0 to 3, wherein a and d are not simultaneously 0; e is an integer of 0 to 3, wherein d+e=3; m is a number of 1 to 2; s is an integer of 1 or more; and t is an integer of 1 or more.

In the formula (1), "n" defines the number of silicon atoms constituting the homocyclic ring and its values is 0 to 5, preferably 1 or more, more preferably 2 or more, and preferably 4 or less, more preferably 3 or less. It is particularly preferable that n is 3, and thus the homocyclic ring is preferably a six-membered silicon homocyclic ring.

In the formula (1), $X^1$ represents a halogen atom bonded to a silicon atom constituting the ring, and $X^2$ represents a halogen atom of a silyl group bonded to a silicon atom constituting the ring. Examples of the halogen atom of $X^1$ and $X^2$ include a chlorine atom, a bromine atom, an iodine atom and a fluorine atom, and among them, a chlorine atom and a bromine atom are preferable, and a chlorine atom is more preferable. In the case that a plurality of $X^1$ are present, the plural X¹ may be the same or different from each other. In the case that a plurality of X² are present, the plural X² may be the same or different from each other.

In the formula (1), "a" represents a number of a halogen atom bonded to silicon atoms constituting the ring, "b" represents a number of a hydrogen atom bonded to silicon atoms constituting the ring, and "c" represents a number of a silyl group bonded to silicon atoms constituting the ring. "d" represents a number of a halogen atom of a silyl group bonded to silicon atoms constituting the ring, and "e" represents a number of a hydrogen atom of the silyl group bonded to silicon atoms constituting the ring. In the case that "c" is 2 or more, plural silyl groups bonded to silicon atoms constituting the ring may be the same or different from each other. "a", "b" and "c" represent integers from 0 to 2n+6, wherein the value of a+b+c is equal to 2n+6 and a and c are not simultaneously 0; and it is preferable that "a" is an integer from 1 to 2n+6 and "b" and "c" are integers from 0 to n+5, and it is more preferable that "a" is an integer of n+6 to 2n+6 and "b" and "c" are integers of 0 to n. In the above formula (1), it is even more preferable that "c" is 0, in respect that side reactions such as a coupling reaction upon the reaction with a Lewis acid compound can be suppressed, storage stability of the salt of the cyclic halosilane compound or the cyclic halosilane compound produced from that is improved, generation of silane gas is suppressed in the reduction step of the cyclic halosilane compound, and yield of the cyclic silane compound can be increased. It is particularly preferable that "a" is 2n+6 and "b" and "c" are 0.

In the formula (1), "L" represents an anionic ligand coordinated to silicon atoms constituting the ring, "p" represents a valence of the ligand, that is an integer of −2 to 0, and "m" represents a number of the ligand, that is a number of 1 to 2. Examples of the anionic ligand include a halide ion, a nitrate ion, a cyanide ion and others.

In the formula (1), "K" represents a counter cation, "q" represents a valence of the counter cation K, that is an integer of 0 to 2, and depending on the valence and the number of the ligand L and the valence of the counter cation K, the values of "s" and "t" are respectively determined. Examples of the counter cation K include oniums (e.g., a phosphonium ion and an ammonium ion), polyamine-SiH₂Cl⁺ (e.g., pedeta-SiH₂Cl⁺, teeda-SiH₂Cl⁺) and others. However, in the case where the counter cation K is polyamine-SiH₂Cl⁺, since pyrophoric silane gas is generated upon the reaction with the Lewis acid compound, an onium is preferably used as the cation K in order to suppress generation of such silane gas. The onium compound is preferably employed as the counter cation K. When the onium is employed as the counter cation K, yield of the cyclic halosilane compound in the decomplexation step is improved, that is also preferable.

As the onium of the counter cation K, a phosphonium ion represented by the following formula (2) and an ammonium ion represented by the following formula (3) are preferable. In the formulas (2) and (3), R¹ to R⁴ and R⁵ to R⁸ each independently represent a hydrogen atom, an alkyl group or an aryl group.

(2)

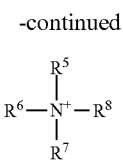

(3)

In the formula (2), R¹ to R⁴ may be different from each other, but preferably they are all the same group. In the formula (3), R⁵ to R⁸ may be different from each other, but preferably they are all the same group. As the alkyl group of R¹ to R⁴ and R⁵ to R⁸, an alkyl group having 1 to 16 carbon atoms such as methyl group, ethyl group, propyl group, butyl group, pentyl group, hexyl group, heptyl group, octyl group and cyclohexyl group is preferable, and an alkyl group having 1 to 8 carbon atoms is more preferable. As the aryl group of R¹ to R⁴ and R⁵ to R⁸, an aryl group having 6 to 18 carbon atoms such as phenyl group and naphthyl group is preferable, and an aryl group having 6 to 12 carbon atoms is more preferable. R¹ to R⁴ and R⁵ to R⁸ are preferably alkyl groups or aryl groups.

Specific examples of the salt of the cyclic halosilane compound represented by the formula (1) include salts of tetradecachlorocyclohexasilane dianion complex ([Si₆Cl₁₄²⁻]), tetradecabromocyclohexasilane dianion complex ([Si₆Br₁₄²⁻]) and others. As the counter ion thereof, a phosphonium ion or an ammonium ion is preferable.

As the salt of the cyclic halosilane compound represented by the formula (1), a compound represented by the following formula (4) or formula (5) is preferably used. When such compound is used as the salt of the cyclic halosilane compound, formation of by-products and generation of pyrophoric silane gas are suppressed upon the reaction of the salt of the cyclic halosilane compound with a Lewis acid compound and the yield of the cyclic hydrogenated silane compound can be easily enhanced. In addition, production of the cyclic halosilane compound is facilitated as described below.

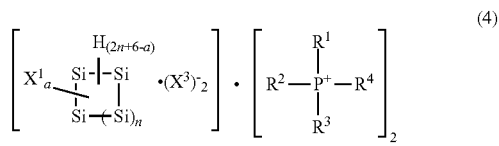

(4)

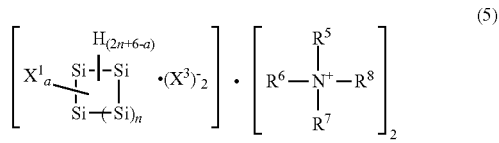

(5)

In the above formulas (4) and (5), X¹, R¹ to R⁴, R⁵ to R⁸, n and a represent the same meanings as the above and X³ represents a halogen atom. In the formulas (4) and (5), X³ exists as an ionic form, namely, a halide ion.

Examples of the halogen atom of X³ include a chlorine atom, a bromine atom, an iodine atom and a fluorine atom, and among them, a chlorine atom and a bromine atom are preferable, and a chlorine atom is more preferable. In the case that a plurality of X³ are present, the plural X³ may be the same or different from each other. X¹ and X³ may be the same or different from each other. In the formulas (4) and (5), when X¹ and X³ are all chlorine atoms, the cyclic hydrogenated silane compounds is able to be produced at low cost.

In the formulas (4) and (5), "n" represents an integer of 0 to 5 and "a" represents an integer of 1 to 2n+6; and among them, "n" is particularly preferably 3, and in this case, "a" is preferably 6 or more, more preferably 9 or more and particularly preferably 12.

The salt of the cyclic halosilane compound may be purified as necessary prior to the reaction with the Lewis acid compound. When the salt of the cyclic halosilane compound is purified to increase the purity, formation of by-products by reaction with the Lewis acid compound can be suppressed. For refining the salt of the cyclic halosilane compound, known purification methods such as solid-liquid separation, distillation (solvent evaporation), crystallization and extraction may be employed.

In the decomplexation step, a free cyclic halosilane compound, that is, a noncomplexed cyclic halosilane compound, can be obtained by contacting the salt of the cyclic halosilane compound with the Lewis acid compound to react. Specifically, when the salt of the cyclic halosilane compound is brought into contact with the Lewis acid compound, the Lewis acid compound acts electrophilically on the anionic ligand contained in the salt of the cyclic halosilane compound to withdraw the anionic ligand from the salt of the cyclic halosilane compound and liberate the counter cation, whereby the corresponding cyclic halosilane compound can be obtained. Such noncomplexed cyclic halosilane compound has higher solvent solubility than the complexed cyclic halosilane compound, and therefore, when the noncomplexed cyclic halosilane compound is brought into contact with a metal hydride in the subsequent reduction step, reduction of the cyclic halosilane compound is able to be carried out in high concentration, and the cyclic hydrogenated silane compound can be efficiently produced.

In the decomplexation step, for example, a cyclic halosilane compound represented by the following formula (6) can be obtained from the salt of the cyclic halosilane compound represented by the above formula (1). In the following formula (6), $X^1$, $X^2$, a to e, and n represent the same meaning as described above.

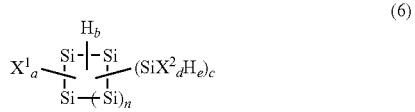

(6)

The kind of the Lewis acid compound is not particularly restricted, and it is preferable to use a metal halide. Examples of the metal halide include metal chlorides, metal bromides, metal iodides and others, and from the viewpoint of reactivity and ease of control of the reaction, a metal chloride is preferably used. Examples of the metal element constituting the metal halide include group 13 elements such as boron, aluminum, gallium, indium and thallium; group 11 elements such as copper, silver and gold; group 4 elements such as titanium and zirconium; iron, zinc, calcium and others. Specific examples of the Lewis acid compound include boron halides such as boron trifluoride, boron trichloride and boron tribromide; aluminum halides such as aluminum chloride and aluminum bromide; gallium halides such as gallium chloride and gallium bromide; indium halides such as indium chloride and indium bromide; thallium halides such as thallium chloride and thallium bromide; copper halides such as copper chloride and copper bromide; silver halides such as silver chloride and silver bromide; gold halides such as gold chloride and gold bromide; titanium halides such as titanium chloride and titanium bromide; zirconium halides such as zirconium chloride and zirconium bromide; iron halides such as iron chloride and iron bromide; zinc halides such as zinc chloride and zinc bromide; calcium halides such as calcium chloride and calcium bromide; and others.

The used amount of the Lewis acid compound may be appropriately adjusted depending on the reactivity of the salt of the cyclic halosilane compound with the Lewis acid compound, and is, for example, preferably 0.5 mol or more, more preferably 1.5 mol or more, and preferably 20 mol or less, more preferably 10 mol or less, relative to 1 mol of the salt of the cyclic halosilane compound.

The reaction of the salt of the cyclic halosilane compound with the Lewis acid compound is preferably carried out in a solvent or a dispersion medium, that are simply referred to as a solvent. Examples of the solvent (reaction solvent) used in the reaction include hydrocarbon solvents such as hexane, toluene, heptane, octane, decane, cyclohexane, cyclooctane and xylene; halogenated hydrocarbon solvents such as dichloromethane and 1,2-dichloroethane; ether solvents such as diethyl ether, tetrahydrofuran, cyclopentyl methyl ether, diisopropyl ether and methyl tertiary-butyl ether; and others. These organic solvents may be used alone or two or more of them may be used in combination. In order to remove water and dissolved oxygen contained in the reaction solvent, it is preferable that the reaction solvent is subjected to purification such as distillation and dehydration prior to the reaction.

The used amount of the reaction solvent is not particularly limited, and it is usually preferably adjusted so that the concentration of the salt of the cyclic halosilane compound is 0.005 mol/L or higher and 10 mol/L or lower, more preferably 0.01 mol/L or higher and 5 mol/L or lower, and even more preferably 0.25 mol/L or higher and 1 mol/L or lower.

A method of contacting the salt of the cyclic halosilane compound with the Lewis acid compound in the reaction solvent is not particularly limited, and examples thereof include, for example, (1) a method of preparing a solution (or dispersion) of the salt of the cyclic halosilane compound and a solution (or dispersion) of the Lewis acid compound by dissolving or dispersing the salt of the cyclic halosilane compound and the Lewis acid compound in a solvent respectively in advance, followed by mixing these solutions (or dispersions); (2) a method of simultaneously or sequentially adding the salt of the cyclic halosilane compound and the Lewis acid compound to a solvent; (3) a method of adding the Lewis acid compound to a solution (or dispersion) of the salt of the cyclic halosilane compound; and (4) a method of preparing the salt of the cyclic halosilane compound and the Lewis acid compound, followed by adding a solvent thereto.

Reaction temperature upon carrying out the reaction of the salt of the cyclic halosilane compound with the Lewis acid compound may be appropriately adjusted depending on the reactivity, and is preferably, for example, −80° C. or higher, more preferably −50° C. or higher, even more preferably −30° C. or higher, and preferably 200° C. or lower, more preferably 150° C. or lower, even more preferably 100° C. or lower.

An atmosphere upon carrying out the reaction of the salt of the cyclic halosilane compound with the Lewis acid compound is not particularly restricted, and from the viewpoint of suppressing oxidation of the cyclic halosilane compound and its salt, the oxygen concentration in the atmosphere is 9% by volume or lower, more preferably 5% by volume or lower, even more preferably 3% by volume or lower, particularly preferably 1% by volume or lower. In addition, from the viewpoint of suppressing hydrolysis of the cyclic halosilane compound and its salt, the moisture concentration in the atmosphere is preferably 2000 ppm (volumetric basis) or lower, more preferably 1500 ppm (volumetric basis) or lower, even more preferably 1000 ppm (volumetric basis) or lower, further even more preferably 500 ppm (volumetric basis) or lower, further even more preferably 150 ppm (volumetric basis) or lower, particularly preferably 10 ppm (volumetric basis) or lower. The reaction of the salt of the cyclic halosilane compound with the Lewis acid compound is preferably carried out in an atmosphere of an inert gas (e.g., nitrogen gas or argon gas), and it is also preferable that the reaction is carry out under light shielding condition.

The cyclic halosilane compound obtained by the reaction of the salt of the cyclic halosilane compound with the Lewis acid compound may be purified as necessary. For the purification of the cyclic halosilane compound, known means such as solid-liquid separation, distillation (solvent evaporation), crystallization and extraction can be employed.

The cyclic halosilane compound obtained in the decomplexation step is reduced by contacting with a metal hydride in the reduction step. Thereby, a cyclic hydrogenated silane compound can be obtained.

The cyclic hydrogenated silane compound is not particularly limited as long as it has a homocyclic ring constituted by liking silicon atoms and is composed of a silicon atom and a hydrogen atom. In the cyclic hydrogenated silane compound, hydrogen atoms may be bonded to all substitution positions of silicon atoms constituting the homocyclic ring, or an unsubstituted silyl group may be bonded to a silicon atom constituting the homocyclic ring. However, from the viewpoint of storage stability, it is preferable that the cyclic hydrogenated silane compound does not contain a silicon atom which does not constitute the homocyclic ring. In the reduction step, since the salt of the cyclic halosilane compound not reduced but the cyclic halosilane compound is reduced, silane gas derived from the counter cation of the salt is not generated and generation of silane gas can be suppressed as a whole. Therefore, the cyclic hydrogenated silane compound can be easily obtained with high yield.

The cyclic hydrogenated silane compound obtained in the reduction step is preferably a compound represented by the formula (7): $Si_zH_{2z}$. In the formula (7), "z" represents a number of silicon atoms constituting the homocyclic ring, and "z" is preferably 3 or more, more preferably 4 or more, even more preferably 5 or more, and preferably 8 or less, more preferably 7 or less, even more preferably 6 or less. From the viewpoint of being useful for preparing of a thin film silicon, it is particularly preferable that the number of silicon atoms constituting the homocyclic ring is 6 (that is, z=6).

From the same viewpoint, the cyclic halosilane compound obtained, for example, in the decomplexation step and subjected to the reduction step is preferably a compound represented by the formula (8): $Si_zX^1_{(2z-a)}H_a$. In this case, it is preferable that 10 mol % or more and 100 mol % or less of the compound represented by the formula (9-1): $Si_zX^1_{2z}$ is included in 100 mol % of the compound represented by the formula (8). The compound represented by the formula (8) may further include a compound represented by the formula (9-2): $Si_zX^1_{(2z-1)}H_1$. In this case, the ratio of the compounds represented by the formula (9-1) and the formula (9-2) in 100 mol % of the compound represented by the formula (8) is, for example, 50 mol % or more, preferably 60 mol % or more. The compound represented by the formula (8) may further include a compound represented by the formula (9-3): $Si_zX^1_{(2z-2)}H_2$. The compounds represented by the formula (9-2) and the formula (9-3) have higher solubility in a solvent, and therefore, from the viewpoint of improving the reduction efficiency, the ratio of the compounds represented by the formula (9-2) and the formula (9-3) in 100 mol % of the compound represented by the formula (8) is preferably 1 mol % or more and 90 mol % or less. In the formulas (8) and (9-1) to (9-3), embodiments of $X^1$ and a and preferred embodiments of them are the same as $X^1$ and a in the above formula (1), unless otherwise mentioned; and embodiments of z and preferred embodiments of that are the same as z in the above formula (7), unless otherwise mentioned.

The kind of the metal hydride used for the reduction of the cyclic halosilane compound is not particularly restricted, and examples thereof include, for example, aluminum hydride compounds such as lithium aluminum hydride, diisobutylaluminum hydride and sodium bis (2-methoxyethoxy) aluminum hydride; boron hydride compounds such as sodium borohydride, lithium triethylborohydride, nickel borohydride and zinc borohydride; tin hydride compounds such as tributyltin hydride; transition metal hydride compounds; and others. These metal hydrides may be used alone, or two or more of them may be used in combination.

The used amount of the metal hydride may be appropriately adjusted, and is preferably adjusted so that the equivalent of hydride of the metal hydride to one silicon-halogen bond contained in the cyclic halosilane compound is, for example, 0.5 equivalent or more, more preferably 0.8 equivalent or more, and even more preferably 0.9 equivalent or more, and preferably 15 equivalents or less, more preferably 5 equivalents or less, even more preferably 4 equivalents or less, further even more preferably 2 equivalents or less. When the amount of the metal hydride is too large, it takes time for the post-treatment and the productivity tends to decrease. Meanwhile, when the amount of the metal hydride is too small, the yield tends to decrease, that is not preferable.

The reduction reaction of the cyclic halosilane compound with the metal hydride is preferably carried out in a solvent (reaction solvent). As the solvent used herein, an organic solvent is preferable, and for example, hydrocarbon solvents such as hexane, toluene, heptane, octane, decane, cyclohexane, cyclooctane and xylene; ether solvents such as diethyl ether, tetrahydrofuran, cyclopentyl methyl ether, diisopropyl ether and methyl tertiary-butyl ether; and others are preferably used. These solvents may be used alone or two or more of them may be used in combination. In order to remove water and dissolved oxygen contained therein, it is preferable that the organic solvent used for the reduction reaction is subjected to purification such as distillation or dehydration prior to the reaction. It is also preferable to use a solvent containing the solvent used in the decomplexation step or use the same solvent as in the decomplexation step.

The amount of the reaction solvent used for the reduction reaction is not particularly limited, and usually it is preferably adjusted so that the concentration of the cyclic halosilane compound is 0.01 mol/L or higher and 1 mol/L or lower. Thus, it is preferable that the cyclic halosilane compound is blended with the solvent so that the concentration of the cyclic halosilane compound is 0.01 mol/L or higher and 1 mol/L or lower and is contacted with the metal hydride. The concentration of that is preferably 0.02 mol/L or higher, more preferably 0.03 mol/L or higher, and 0.7 mol/L or lower, more preferably 0.5 mol/L or lower. When the concentration of the cyclic halosilane compound is higher than that range, that is, when the used amount of the reaction solvent is too small, heat generated by the reduction reaction is not sufficiently removed, and there is a possibility that problems such as decrease in reaction rate due to difficulty of dissolution of the reactant may occur. Meanwhile, when the concentration of the cyclic halosilane compound is lower than that range, that is, when the used amount of the reaction solvent is too large, the amount of the solvent to be distilled off increases in the case that, for example, the reaction product is purified by distillation after the reduction reaction, and the productivity tends to decrease.

The reduction reaction can be conducted by contacting the cyclic halosilane compound with the metal hydride. Contacting the cyclic halosilane compound with the metal hydride is preferably conducted in the presence of a solvent (reaction solvent). Examples of a method of contacting the cyclic halosilane compound with the metal hydride in a solvent include, for example, (1) a method of dissolving or dispersing one of the cyclic halosilane compound and the metal hydride in a solvent to prepare a solution or dispersion and mixing it with the other of them (specifically, adding the other of them to the solution or dispersion or adding the solution or dispersion to the other of them); (2) a method of dissolving or dispersing each of them to a solvent to prepare solutions or dispersions, followed by mixing them; and (3) a method of simultaneously or sequentially adding the cyclic halosilane compound and the metal hydride to a solvent. Among them, the method (2) is a particularly preferable embodiment.

In contacting the cyclic halosilane compound with the metal hydride, it is preferable that at least one (i.e., one or both) of the cyclic halosilane compound and the metal hydride is sequentially fed to a reaction system for conducting the reduction. When one or both of the cyclic halosilane compound and the metal hydride sequentially is fed in this manner, heat generated in the reduction reaction is able to be controlled by adjusting the feeding rate and others; and therefore, an effect that leads to an improvement in productivity such as miniaturization of a condenser and the like can be obtained. In addition, it is also possible to obtain the effect of suppressing the formation of by-products and improving the reaction yield. In the sequential addition, it may be fed continuously or dividedly, and is preferable to be fed continuously.

In the case where one of the cyclic halosilane compound and the metal hydride is sequentially fed, the other of them may be prepared in the reaction system (a reactor) with a solvent or singly, namely, without solvent. In the case where both of them are sequentially fed, only a solvent may be prepared in advance in the reaction system (a reactor), or the cyclic halosilane compound and the metal hydride may be simultaneously or sequentially fed to an empty reactor. In either case, it is preferable that the feeding substance, that is the cyclic halosilane compound and/or the metal hydride, is dissolved or dispersed in a solvent and is fed in the form of a solution or a dispersion.

In the producing process of the present invention, since the reduction is carried out on a free cyclic halosilane compound, that is, the noncomplexed cyclic halosilane compound, in the reduction step, solubility (or dispersibility) in a solvent tends to be improved in comparison with the case of the reduction on a complexed cyclic halosilane compound, that is, the salt of the cyclic halosilane compound. Therefore, the reactant concentration in the reduction step can be set higher, that enables remarkable improvement in production efficiency of the cyclic hydrogenated silane compound and adoption of various production processes. For example, in the case that the reduction reaction is carried out by sequentially feeding at least one of the cyclic halosilane compound and the metal hydride to the reaction system in which the reduction is performed, as described above, a low solubility (or a low dispersibility) of the cyclic halosilane compound leads to a decrease in production efficiency since the cyclic halosilane compound has to react with the metal hydride at a low concentration in the reaction system. Meanwhile, in the producing process of the present invention, since dissolution (or dispersibility) of the cyclic halosilane compound in a solvent is good, the concentration of the cyclic halosilane compound can be increased and the production efficiency can be improved. In addition, the metal hydride is desired to be handled in the form of a solution or the like at the lowest concentration due to its pyrophoric property; and in the present invention, since the concentration of the cyclic halosilane compound can be increased, even if the concentration of the metal hydride solution is set relatively low, the reactant concentration can be high as a whole. Therefore, it is possible to improve production efficiency while taking safety into consideration.

As preferred embodiments of the method of sequentially feeding one or both of the cyclic halosilane compound and the metal hydride, the following three embodiments are shown: (A) a method of preparing a solution or dispersion of the cyclic halosilane compound in a reactor and adding a solution or dispersion of the metal hydride thereto sequentially; (B) a method of preparing a solution or dispersion of the metal hydride in a reactor and adding a solution or dispersion of the cyclic halosilane compound thereto sequentially; and (C) a method of feeding a solution or dispersion of the cyclic halosilane compound and a solution or dispersion of the metal hydride to a reactor simultaneously or sequentially. Among them, it is preferable to adopt the above method (A) or (B) from the viewpoint of easy control of the heat generated in the reduction reaction and stable production. In the present invention, since the solubility (or dispersibility) of the cyclic halosilane compound in a solvent is good, the concentration of the cyclic halosilane compound solution (or dispersion) can be set high. Therefore, precipitation or deposition in the feed line of the cyclic halosilane compound can be suppressed, that enables stable production, while improving the production efficiency of the cyclic hydrogenated silane compound.

In the case where one or both of the cyclic halosilane compound and the metal hydride is fed in the above embodiments (A) to (C), the solute concentration in the solution or dispersion containing the cyclic halosilane compound as a solute is preferably 0.01 mol/L or higher, more preferably 0.02 mol/L or higher, even more preferably 0.04 mol/L or higher, particularly preferably 0.05 mol/L or higher. When the solute concentration is too low, the amount of the solvent to be distilled off at a time of isolating the target product increases and the productivity tends to decrease. Meanwhile, the upper limit of the solute concentration in the solution or dispersion containing the cyclic halosilane compound as a solute is preferably 1 mol/L or lower, more preferably 0.8 mol/L or lower, even more preferably 0.5 mol/L or lower. When the solute concentration (particularly the solute concentration of the solution or dispersion to be sequentially added) is too high, it tends to be difficult to control the heat generated in the reduction reaction. It is preferable that the solute concentration in the solution or dispersion containing the cyclic halosilane compound as a solute and the solute concentration in the solution or dispersion containing the metal hydride as a solute are set so that the amounts of the both solvents are almost equal to each other or the amount of the solvent in the solution or dispersion containing the cyclic halosilane compound as a solute is larger than that in the solution or dispersion containing the metal hydride as a solute.

In the case where one or both of the cyclic halosilane compound and the metal hydride is fed in the above embodiments (A) to (C), temperature at the time of feeding (specifically the temperature of the solution or dispersion to be sequentially added and/or the temperature of the solution or dispersion prepared in the reactor) is preferably −80° C. or higher, more preferably −50° C. or higher, even more preferably −30° C. or higher, and preferably 80° C. or lower, more preferably 50° C. or lower, even more preferably 40° C. or lower. The feeding rate is preferably 0.01 mL/min or more, more preferably 0.1 mL/min or more, even more preferably 1 mL/min or more, and preferably 1000 mL/min or less, more preferably 500 mL/min or less, even more preferably 200 mL/min or less, though it depends on the solute concentration in the solution or dispersion. The feeding time in this case is not particularly limited, and from the viewpoint of the productivity and the reactivity, it is preferably 10 minutes or longer, more preferably 30 minutes or longer, even more preferably 1 hour or longer, and preferably 20 hours or shorter, more preferably 10 hours or shorter, even more preferably 6 hours or shorter.

Reaction temperature upon conducting the reduction reaction may be appropriately adjusted according to the reactivity, and it is preferably −20° C. or higher, more preferably −10° C. or higher, even more preferably 0° C. or higher, and preferably 150° C. or lower, more preferably 100° C. or lower, even more preferably 80° C. or lower, particularly preferably 70° C. or lower. Reaction time may be appropriately adjusted according to the progress of the reaction, and it is preferably, for example, 10 minutes or longer, more preferably 1 hour or longer, even more preferably 2 hours or longer, and preferably 72 hours or shorter, more preferably 48 hours or shorter, even more preferably 24 hours or shorter.

The cyclic hydrogenated silane compound is an oxygen-prohibiting substance. Therefore, the reduction reaction is preferably conducted in an inert gas atmosphere such as nitrogen gas and argon gas.

In the reduction step, the total concentration of the cyclic halosilane compound and the cyclic hydrogenated silane compound in the reaction solution at the end of the reduction reaction is preferably 0.01 mol/L or higher, more preferably 0.02 mol/L or higher, even more preferably 0.04 mol/L or higher, further even more preferably 0.05 mol/L or higher, and preferably 1 mol/L or lower, more preferably 0.8 mol/L or lower, even more preferably 0.5 mol/L or lower, further even more preferably 0.3 mol/L or lower. Thereby, it becomes easier to control the heat generated in the reduction reaction while improving the production efficiency of the cyclic hydrogenated silane compound. At the end of the reduction reaction, the concentration of the cyclic halosilane compound in the reaction solution may be 0 mol/L.

The cyclic hydrogenated silane compound obtained by the reduction reaction may be purified for increasing the purity. As a purification method of the cyclic hydrogenated silane compound, known purification methods such as solid-liquid separation, distillation, crystallization and extraction can be adopted. For example, in the reaction solution, low-boiling impurities having a boiling point lower than the cyclic silane compound or high-boiling impurities having a boiling point higher than the cyclic silane compound may be dissolved, in addition to the cyclic hydrogenated silane compound. Therefore, in order to separate the cyclic hydrogenated silane compound from low-boiling impurities or high-boiling impurities and to obtain a cyclic silane compound with high purity, distillation is preferably conducted. Temperature for the distillation may be appropriately set according to the composition of the cyclic hydrogenated silane compound and the impurities contained in the reaction solution.

In the producing process of the present invention, though the salt of the cyclic halosilane compound used in the decomplexation step can be produced by contacting a halosilane compound with a tertiary polyamine, it is preferably produced by contacting a halosilane compound with at least one of a phosphonium salt and an ammonium salt. In this respect, the process for producing a cyclic halosilane compound of the present invention comprises a step of contacting a halosilane compound with at least one of a phosphonium salt and an ammonium salt, thereby obtaining the salt of the cyclic halosilane compound (a cyclization coupling step).

In the cyclization coupling step, a cyclization coupling reaction of a halosilane compound occurs by bringing the halosilane compound into contact with at least one of a phosphonium salt and a ammonium salt, thereby obtaining the salt of the cyclic halosilane compound which contains a ring formed by linking silicon atoms of the halosilane compound. In this case, the obtained salt of the cyclic halosilane compound has a phosphonium ion or an ammonium ion as a counter cation (that is, a phosphonium salt or an ammonium salt) and the counter cation does not contain a silicon atom; and therefore, generation of silane gas derived from the counter cation can be suppressed at the time of reacting with the Lewis acid compound in the decomplexation step, and the production of the cyclic halosilane compound is facilitated. In this respect, even in the case where a tertiary polyamine is used in the cyclization coupling step, it is preferable that the used amount of the tertiary polyamine should be minimized, and for example, the used amount of the tertiary polyamine is preferably 0 mol % to 1 mol %, relative to the total used amount of the phosphonium salt and the ammonium salt, and more preferably a tertiary polyamine is not used.

As the halosilane compound of a raw material, a disilane halide such as hexachlorodisilane, hexabromodisilane and hexaiododisilane can be used, however, it is preferable to use a monosilane compound (a halogenated monosilane compound). Examples of the monosilane compound include, for example, trihalogenated silanes such as trichlorosilane, tribromosilane, triiodosilane and trifluorosilane; dihalogenated silanes such as dichlorosilane, dibromosilane, diiodosilane and difluorosilane; tetrahalogenated silanes such as tetrachlorosilane, tetrabromosilane, tetraiodosilane and tetrafluoro silane; and others. Among them, trihalogenated silane is preferable, and trichlorosilane is more preferable.

When the halogenated monosilane compound is used as the halosilane compound, it becomes possible to produce the salt of the cyclic halosilane compound which does not contain a silicon atom other than silicon atoms constituting the ring structure. Since the salt of the cyclic halosilane compound and the halosilane compound produced therefrom are relatively excellent in storage stability and chemical stability, formation of by-products due to its decomposition can be suppressed during storage or upon the reaction with the Lewis acid compound in the decomplexation step. Therefore, it becomes possible to suppress generation of silane gas or adverse influences (for example, a polymerization reaction and a coupling reaction) due to by-products, during storage, decomplexation step and reduction step; and as a result, the yield of the cyclic hydrogenated silane compound remarkably tends to be improved. Further, since a purification step for removing the by-products can be simplified, the production efficiency is improved.

The phosphonium salt is preferably a quaternary phosphonium salt, and a salt represented by the following formula (10) is preferably indicated. The ammonium salt is preferably a quaternary ammonium salt, and a salt represented by the following formula (11) is preferably indicated. In the formulas (10) and (11), embodiments of $R^1$ to $R^4$ and $R^5$ to $R^8$ and preferred embodiments of them are the same as in the above formulas (2) and (3), unless otherwise mentioned, and $A^-$ represents a monovalent anion.

(10)

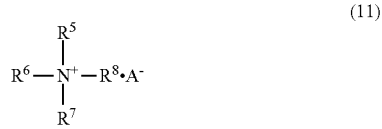

(11)

Examples of the monovalent anion represented by $A^-$ in the formulas (10) and (11) include halide ions (e.g., $Cl^-$, $Br^-$, $I^-$ and others), borate ions (e.g., $BF_4^-$), phosphorus anions (for example, $PF_6^-$), and others. Among them, from the viewpoint of ease of availability, $Cl^-$, $Br^-$ and $I^-$ are preferable, and $Cl^-$ and $Br^-$ are particularly preferable.

In the cyclization coupling step, either one of the phosphonium salt and the ammonium salt may be used, or both of them may be used. Regarding the phosphonium salt, only one kind of that may be used, or two or more kinds of that may be used in combination. Regarding the ammonium salt, only one kind of that may be used, or two or more kinds of that may be used in combination.

In the formula (10), $R^1$ to $R^4$ may be different from each other, but preferably they are all the same group. In the formula (11), $R^5$ to $R^8$ may be different from each other, but preferably they are all the same group. As described above, $R^1$ to $R^4$ and $R^5$ to $R^8$ are preferably an alkyl group or an aryl group.

By using the phosphonium salt represented by the formula (10) or the ammonium salt represented by the formula (11), the salt of the cyclic halosilane compound represented by the formula (4) or the formula (5) can be obtained, and in particular, a salt of a cyclic halosilane compound which has a six-membered silicon homocyclic ring and does not contain a silicon atom other than silicon atoms constituting this homocyclic ring can be easily obtained. For example, in the case that trichlorosilane is used as the halosilane compound and a phosphonium salt represented by the formula (10) wherein $A^-$ is chlorine ion ($Cl^-$) is used as the phosphonium salt, a salt of a cyclic halosilane compound dianion and a phosphonium ion such as dodecachlorodihydrocyclohexasilane dianion ($[Ph_4P^+]_2[Si_6H_2Cl_{12}]^{2-}$) salt, tridecachlorohydrocyclohexasilane dianion ($[Ph_4P^+]_2[Si_6HCl_{13}]^{2-}$) salt and tetradecachlorocyclohexasilane dianion ($[Ph_4P^+]_2[Si_6Cl_{14}]^{2-}$) salt is obtained.

The used amount of the phosphonium salt and/or the ammonium salt, that means a total used amount thereof in the case where two or more kinds of the salt are used, is preferably 0.01 mol or more, more preferably 0.05 mol or more, even more preferably 0.08 mol or more, and preferably 1.0 mol or less, more preferably 0.7 mol or less, even more preferably 0.5 mol or less, relative to 1 mol of the halosilane compound. When the amount of the phosphonium salt and/or the ammonium salt is too small, the halosilane compound may remain to be unreacted and the yield of the salt of the cyclic halosilane compound is likely to decrease. Meanwhile, when the amount of the phosphonium salt and/or the ammonium salt is too large, purity of the salt of the cyclic halosilane compound is likely to decrease.

The cyclization coupling reaction is preferably carried out in the presence of a chelate ligand such as a polyether compound, a polythioether compound and a polydentate phosphine compound. When the cyclization coupling reaction is carried out in the presence of a chelate ligand, the salt of the cyclic halosilane compound can be efficiently produced. In addition, by appropriately selecting a kind of the chelate ligand to be used, the number of hydrogen atom or the composition ratio in the obtained cyclic halosilane compound can be adjusted.

Examples of the polyether compound include, for example, dialkoxyalkanes such as 1,1-dimethoxyethane, 1,2-dimethoxyethane, 1,2-diethoxyethane, 1,2-dipropoxyethane, 1,2-diisopropoxyethane, 1,2-dibutoxyethane, 1,2-diphenoxyethane, 1,3-dimethoxypropane, 1,3-diethoxypropane, 1,3-dipropoxypropane, 1,3-diisopropoxypropane, 1,3-dibutoxypropane, 1,3-diphenoxypropane, 1,4-dimethoxybutane, 1,4-diethoxybutane, 1,4-dipropoxybutane, 1,4-diisopropoxybutane, 1,4-dibutoxybutane and 1,4-diphenoxybutane. Among them, 1,2-dimethoxyethane is particularly preferable. Examples of the polythioether compound include those in which oxygen atom of the polyether compounds exemplified above is substituted with sulfur atom.

Examples of the phosphine compound include, for example, bis (dialkylphosphino) alkanes such 1,2-bis (dimethylphosphino) ethane, 1,2-bis (diethylphosphino) ethane, 1,2-bis (dipropylphosphino) ethane, 1,2-bis (dibutylphosphino) ethane, 1,2-bis (diphenylphosphino) ethane, 1,3-bis (dimethylphosphino) propane, 1,3-bis (diethylphosphino) propane, 1,3-bis (dipropylphosphino) propane, 1,3-bis (dibutylphosphino) propane, 1,3-bis (diphenylphosphino) propane, 1,4-bis (dimethylphosphino) butane, 1,4-bis (diethylphosphino) butane, 1,4-bis (dipropylphosphino) butane, 1,4-bis (dibutylphosphino) butane and 1,4-bis (diphenylphosphino) butane, and bis (diarylphosphino) alkanes. Among them, 1,2-bis (diphenylphosphino) ethane is particularly preferable.

The used amount of the chelate ligand may be appropriately adjusted, and is preferably 0.01 mol or more, more preferably 0.05 mol or more, even more preferably 0.1 mol or more, and preferably 50 mol or less, more preferably 40 mol or less, even more preferably 30 mol or less, relative to 1 mol of the halosilane compound.

The cyclization coupling reaction is preferably carried out in the presence of a basic compound. Examples of the basic compound include, for example, (mono-, di-, tri-, poly-) amine compounds, and among them, a monoamine compound is preferably used. Specifically, triethylamine, tripropylamine, tributylamine, trioctylamine, triisobutylamine, triisopentylamine, diethylmethylamine, diisopropylethylamine, dimethylbutylamine, dimethyl-2-ethylhexylamine, diisopropyl-2-ethylhexylamine, methyldioctylamine and others are preferable, and triethylamine and diisopropylethylamine are particularly preferable. Regarding the basic compound, only one kind of that may be used, or two or more kinds of that may be used in combination.

The used amount of the basic compound, that means a total used amount thereof in the case where two or more kinds of that are used, may be appropriately adjusted according to the kind thereof or the like. For example, in the case of using a monoamine compound, it is preferably 0.1 mol or more, more preferably 0.2 mol or more, even more preferably 0.4 mol or more, and preferably 2 mol or less, more preferably 1.8 mol or less, even more preferably 1.5 mol or less, relative to 1 mol of the halosilane compound. When the amount of the basic compound (the monoamine compound) is too small, the halosilane compound may remain to be unreacted and the yield of the salt of the cyclic halosilane compound is likely to decrease. Meanwhile, when the amount of the basic compound (the monoamine compound) is too large, decrease in the yield or purity of the salt of the cyclic halosilane compound is likely to be caused. A diamine compound, a triamine compound or a polyamine compound can be used as the basic compound, and in this case, the used amount (or the total used amount) of the basic compound (di-, tri-, poly-amine) is preferably 0.5 mol or less, more preferably 0.4 mol or less, even more preferably 0.3 mol or less, relative to 1 mol of the halosilane compound, from the viewpoint of suppressing by-production of impurities derived from the polyamine.

The cyclization coupling reaction is preferably carried out in a solvent (reaction solvent). As the reaction solvent, an organic solvent is preferably used. As the organic solvent, a solvent which does not interfere with the cyclization coupling reaction is preferably used, and preferable example of the organic solvent include, for example, halogenated hydrocarbon solvents such as chloroform, dichloromethane and 1,2-dichloroethane; hydrocarbon solvents such as hexane, toluene, heptane, octane, decane, cyclohexane and xylene; ether solvents such as diethyl ether, tetrahydrofuran, cyclopentyl methyl ether, diisopropyl ether and methyl tertiary-butyl ether; aprotic polar solvents such as acetonitrile and N,N-dimethylformamide. Among them, chlorinated hydrocarbon solvents such as chloroform, dichloromethane and 1,2-dichloroethane are preferably used, and 1,2-dichloroethane is particularly preferable.

The amount of the solvent used for the cyclization coupling reaction is not particularly limited, and usually, it is adjusted so that the concentration of the halosilane compound is preferably 0.5 mol/L to 10 mol/L, more preferably 0.8 mol/L to 8 mol/L, and even more preferably 1 mol/L to 5 mol/L.

Reaction temperature upon conducting the cyclization coupling reaction may be appropriately adjusted according to the reactivity, and is, for example about 0° C. to 120° C., preferably about 15° C. to 70° C. The reaction temperature means a solution temperature in the reactor. For adjusting the reaction temperature, a medium for temperature adjustment may be supplied in a jacket provided around the reactor, for example, though it is not limited thereto. Reaction time may be appropriately adjusted according to the progress of the reaction, and is preferably, for example, 1 hour or longer, more preferably 2 hours or longer, even more preferably 3 hours or longer, and preferably 48 hours or shorter, more preferably 24 hours or shorter. During the reaction, stirring may be conducted simultaneously with heating in order to accelerate the reaction.

It is desirable that the cyclization coupling reaction is carried out under substantially anhydrous conditions, and it is preferable to be carried out under an atmosphere of a dry gas (especially an inert gas such as nitrogen gas and argon gas), for example.

The salt of the cyclic halosilane compound obtained by the cyclization coupling step can be isolated from the reaction solution by using purification means such as solid-liquid separation, distillation, crystallization and extraction. Particularly, in the case where the substituents $R^1$ to $R^4$ of the phosphonium salt and the substituents $R^5$ to $R^8$ of the ammonium salt are aryl groups, the salt of the cyclic halosilane compound can be easily purified by solid-liquid separation, since the salt of the cyclic halosilane compound precipitates in the reaction solution. For the same reason, the salt of the cyclic halosilane compound is preferably the phosphonium salt rather than the ammonium salt. In this case, the solid-liquid separation means is not particularly limited, and known solid-liquid separation means such as filtration, precipitation, centrifugation and decantation can be employed.

The present invention has been described above, however, it goes without saying that a combination of two or more individual preferred embodiments of the present invention described above is also a preferred embodiment of the present invention.

According to the present invention, a cyclic hydrogenated silane compound can be efficiently produced. The cyclic hydrogenated silane compound is useful as, for example, a silicon raw material used for a solar cell, a semiconductor and others. In the field of semiconductors, it can also be used for manufacturing SiGe compounds or SiGe films by mixing or reacting with Ge compounds.

EXAMPLES

The present invention is hereinafter described more specifically by reference to Examples; however, the scope of the present invention is not limited to these Examples, and of course, it is possible to implement the invention with appropriate modifications within a range that can conform to the gist of the foregoing and the following, that are all included in the technical scope of the present invention.

(1) Preparation Example 1

(1-1) Preparation of a Salt of a Cyclic Halosilane Dianion

The atmosphere in a 300 mL four-necked flask equipped with a thermometer, a condenser, a dropping funnel and a stirrer was replaced with nitrogen gas, and 11.9 g (0.032 mol) of tetraphenylphosphonium chloride, 2.97 g (0.033 mol) of 1,2-dimethoxyethane, 12.6 g (0.097 mol) of diisopropylethylamine and 100 mL of 1,2-dichloroethane were fed into the flask. Subsequently, while stirring the solution in the flask, 26.8 g (0.198 mol) of trichlorosilane was slowly added dropwise from the dropping funnel at a temperature of 25° C. After completion of the dropwise addition, the resultant was stirred for 2 hours as it was and then stirred while heating at 50° C. for 8 hours to carry out the cyclization coupling reaction. After the reaction, the thus obtained solid was filtered and purified, thereby obtaining a white solid containing 90% by mass of a mixture including a phosphonium salt of dodecachlorodihydrocyclohexasilane dianion ($[Ph_4P^+]_2[Si_6H_2Cl_{12}^{2-}]$), a phosphonium salt of tridecachlorohydro cyclohexasilane dianion ($[Ph_4P^+]_2[Si_6HCl_{13}^{2-}]$) and a phosphonium salt of tetradecachlorocyclohexasilane dianion ($[Ph_4P^+]_2[Si_6Cl_{14}^{2-}]$) in a mass ratio of 4:5:1.

(1-2) Preparation of a Cyclic Halosilane Compound

Under a nitrogen atmosphere, 4.2 g of the white solid obtained in the above (1-1) and 1.0 g of powdered aluminum chloride ($AlC_3$) were fed in a 300 mL three-necked flask equipped with a stirrer, and 50 mL of benzene was added thereto. In a light-shielded state, reaction was carried out while stirring at room temperature for 4 days, and then benzene was distilled off under reduced pressure from the obtained reaction solution, thereby obtaining a white solid. 33 g of hexane was added to the obtained white solid and thus obtained solution was filtered to give a colorless and transparent filtrate. From this filtrate, hexane was distilled off under reduced pressure to obtain 1.7 g of a white solid. By analyzing this white solid with $^{29}$Si-NMR, it was confirmed that $Si_6Cl_2$ was formed.

$Si_6Cl_{12}$: $^{29}$Si-NMR (119 MHz, $C_6D_6$) δ=−3.0

(1-3) Preparation of a Cyclic Hydrogenated Silane Compound 0.7 g (1.2 mmol) of the white solid of $Si_6Cl_{12}$ obtained in the above (1-2) and 65 mL of benzene were fed in a 100 mL three-necked flask equipped with a dropping funnel and a stirrer. After replacing the atmosphere in the flask with nitrogen gas, 17 mL of a diethyl ether solution of lithium aluminum hydride (concentration: about 1.0 mol/L) as a reducing agent was slowly added dropwise from the dropping funnel over 20 minutes at 0° C. while stirring the solution in the flask and then the solution was stirred at 25° C. for 1 hour, thereby carrying out the reduction reaction. After the reaction, the obtained reaction solution was filtered under a nitrogen atmosphere to remove the formed salt. From the obtained filtrate, the solvent was distilled off under reduced pressure, and filtration and purification were conducted to obtain a colorless transparent liquid. By analyzing this liquid, it was confirmed that cyclohexasilane was formed (yield 80%).

(2) Preparation Example 2

(2-1) Preparation of a Cyclic Halosilane Compound

Under a nitrogen atmosphere, 5.0 g of the white solid obtained in the above (1-1) and 1.2 g of powdered aluminum chloride ($AlCl_3$) were fed in a 300 mL three-necked flask equipped with a stirrer, and 100 mL of benzene was added thereto. In a light-shielded state, reaction was carried out while stirring at room temperature for 1 hour, and then benzene was distilled off under reduced pressure from the obtained reaction solution, thereby obtaining a white solid. 100 mL of hexane was added to the obtained white solid and thus obtained solution was filtered to give a colorless and transparent filtrate. From this filtrate, hexane was distilled off under reduced pressure to obtain 1.8 g of a white solid. By analyzing this white solid with $^{29}$Si-NMR, it was confirmed that $Si_6Cl_{12}$ was formed.

(2-2) Preparation of a Cyclic Hydrogenated Silane Compound 1.8 g (3.2 mmol) of the white solid of $Si_6Cl_{12}$ obtained in the above (2-1) and 45 mL of benzene were fed in a 100 mL three-necked flask equipped with a dropping funnel and a stirrer. After replacing the atmosphere in the flask with nitrogen gas, 14 mL of a diethyl ether solution of lithium aluminum hydride (concentration: about 1.0 mol/L) as a reducing agent was slowly added dropwise from the dropping funnel over 20 minutes at 0° C. while stirring the solution in the flask and then the solution was stirred at 25° C. for 3 hours, thereby carrying out the reduction reaction. After the reaction, the obtained reaction solution was filtered under a nitrogen atmosphere to remove the formed salt. From the obtained filtrate, the solvent was distilled off under reduced pressure, and filtration and purification were conducted to obtain a colorless transparent liquid. By analyzing this liquid, it was confirmed that cyclohexasilane was formed (yield 80%).

The invention claimed is:

1. A process for producing a cyclic hydrogenated silane compound, comprising:
   a decomplexation step of contacting a salt of a cyclic halosilane compound with a Lewis acid compound to react, thereby obtaining a cyclic halosilane compound; and
   a reduction step of contacting the cyclic halosilane compound with a metal hydride to reduce the cyclic halosilane compound, thereby obtaining a cyclic hydrogenated silane compound,
   wherein the salt of the cyclic halosilane compound is a compound represented by the following formula (1):

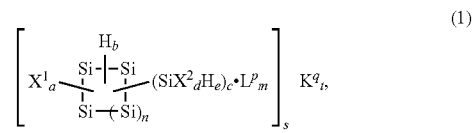

(1)

wherein in the formula (1), $X^1$ and $X^2$ each independently represent a halogen atom; L represents an anionic ligand; p is an integer of −2 to 0 as a valence of the ligand L; K represents a counter cation; q is an integer of 0 to 2 as a valence of the counter cation K; n is an integer of 0 to 5; a, b and c are integers of 0 to 2n+6, wherein a+b+c=2n+6 but a and c are not simultaneously 0; d is an integer of 0 to 3, wherein a and d are not simultaneously 0; e is an integer of 0 to 3, wherein d+e=3; m is a number of 1 to 2; s is an integer of 1 or more; and t is an integer of 1 or more, and
   wherein the cyclic halosilane compound is a compound represented by the following formula (6):

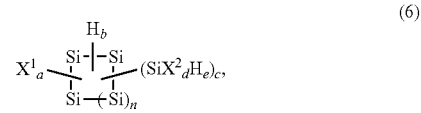

(6)

wherein in the formula (6), $X^1$, $X^2$, a to e and n represent the same meanings as the above.

2. The process for producing a cyclic hydrogenated silane compound according to claim 1, wherein the cyclic halosilane compound is blended with a solvent so that a concentration of the cyclic halosilane compound is 0.02 mol/L or higher and is contacted with the metal hydride in the reduction step.

3. The process for producing a cyclic hydrogenated silane compound according to claim 1, wherein a used amount of the metal hydride is adjusted so that an equivalent of hydride of the metal hydride to one silicon-halogen bond contained in the cyclic halosilane compound is 0.5 equivalent or more and 15 equivalents or less.

4. The process for producing a cyclic hydrogenated silane compound according to claim 1, wherein a total concentration of the cyclic halosilane compound and the cyclic hydrogenated silane compound in a reaction solution at the end of the reduction reaction is 0.02 mol/L or higher and 1 mol/L or lower.

5. The process for producing a cyclic hydrogenated silane compound according to claim 1, further comprising a cyclization coupling step of contacting a halogenated monosilane compound with at least one of a phosphonium salt and an ammonium salt, thereby obtaining the salt of the cyclic halosilane compound.

6. The process for producing a cyclic hydrogenated silane compound according to claim 1, wherein the Lewis acid compound is at least one compound selected from the group consisting of boron halide, aluminum halide, gallium halide, indium halide, thallium halide, copper halide, silver halide, gold halide, titanium halide, zirconium halide, iron halide, zinc halide and calcium halide.

7. The process for producing a cyclic hydrogenated silane compound according to claim 1, wherein the metal hydride is at least one compound selected from the group consisting of an aluminum hydride compound, a boron hydride compound, a tin hydride compound and a hydrogenated transition metal compound.

8. The process for producing a cyclic hydrogenated silane compound according to claim 1, wherein the salt of the cyclic halosilane compound is a salt selected from a tetradecachlorohexasilane dianion complex or a salt of a tetradecabromocyclohexasilane dianion complex.

* * * * *